US012793579B2

(12) United States Patent
Schieber et al.

(10) Patent No.: US 12,793,579 B2
(45) Date of Patent: Nov. 10, 2026

(54) SYNTHETIC EYE MODEL FOR OCULAR IMPLANT SURGICAL TRAINING

(71) Applicant: Alcon Inc., Fribourg (CH)

(72) Inventors: Andrew T. Schieber, Tustin, CA (US); Hector Truong, Westminster, CA (US); Shane Sussman, Laguna Niguel, CA (US); Liam Dunphy, Laguna Niguel, CA (US)

(73) Assignee: Alcon Inc., Fribourg (CH)

( * ) Notice: Subject to any disclaimer, the term of this patent is extended or adjusted under 35 U.S.C. 154(b) by 1273 days.

(21) Appl. No.: 17/640,018

(22) PCT Filed: Sep. 18, 2020

(86) PCT No.: PCT/US2020/051498
§ 371 (c)(1),
(2) Date: Mar. 3, 2022

(87) PCT Pub. No.: WO2021/055751
PCT Pub. Date: Mar. 25, 2021

(65) Prior Publication Data

US 2022/0313490 A1 Oct. 6, 2022

Related U.S. Application Data

(60) Provisional application No. 62/902,274, filed on Sep. 18, 2019.

(51) Int. Cl.
*G09B 23/34* (2006.01)
*G09B 23/28* (2006.01)
(Continued)

(52) U.S. Cl.
CPC ............. *G09B 23/34* (2013.01); *G09B 23/28* (2013.01); *G09B 23/30* (2013.01); *G09B 23/32* (2013.01);
(Continued)

(58) Field of Classification Search
None
See application file for complete search history.

(56) References Cited

U.S. PATENT DOCUMENTS

| | | | |
|---|---|---|---|
| 703,296 | A | 6/1902 | Arnold |
| 1,601,709 | A | 10/1926 | Windom |

(Continued)

FOREIGN PATENT DOCUMENTS

| | | | |
|---|---|---|---|
| AU | 1998/76197 B2 | 2/1999 | |
| DE | 4226476 C1 | 8/1993 | |

(Continued)

OTHER PUBLICATIONS

Bahler, et al.; Trabecular bypass stents decrease intraocular pressure in cultured human anterior segments; Amer. Journal of Ophthalmology; vol. 138, No. 6; pp. 988-994.e2; Dec. 2004.

(Continued)

*Primary Examiner* — Rebecca S Preston

(57) ABSTRACT

A synthetic eye model is provided which can include a number of features. In one embodiment, the synthetic eye can include a rigid or semi-rigid eye shell, a synthetic iris base positioned within the eye shell, an eye core positioned within the eye shell and encircling the synthetic iris base, the eye core including a channel integral to the eye core configured to replicate Schlemm's canal of a human eye, and a synthetic trabecular meshwork tissue coupled to the eye shell and extending across the channel. Methods of using the synthetic eye model are provided, including using the synthetic eye model as a surgical training tool.

14 Claims, 9 Drawing Sheets

(51) Int. Cl.

| | |
|---|---|
| ***G09B 23/30*** | (2006.01) |
| ***G09B 23/32*** | (2006.01) |
| *A61F 9/00* | (2006.01) |
| *A61F 9/007* | (2006.01) |

(52) U.S. Cl.

CPC ......... *A61F 9/0017* (2013.01); *A61F 9/00781* (2013.01); *A61F 2250/0067* (2013.01); *A61M 2210/0612* (2013.01)

(56) References Cited

U.S. PATENT DOCUMENTS

| | | | |
|---|---|---|---|
| 2,716,983 | A | 9/1955 | George et al. |
| 3,071,135 | A | 1/1963 | Baldwin et al. |
| 3,788,327 | A | 1/1974 | Donowitz et al. |
| 3,811,442 | A | 5/1974 | Maroth |
| 3,858,577 | A | 1/1975 | Bass et al. |
| 3,884,236 | A | 5/1975 | Krasnov |
| 3,948,271 | A | 4/1976 | Akiyama |
| 3,982,541 | A | 9/1976 | L'Esperance |
| 4,037,604 | A | 7/1977 | Newkirk |
| 4,134,405 | A | 1/1979 | Smit |
| 4,273,109 | A | 6/1981 | Enderby |
| 4,391,275 | A | 7/1983 | Fankhauser et al. |
| 4,428,746 | A | 1/1984 | Mendez |
| 4,457,757 | A | 7/1984 | Molteno |
| 4,461,294 | A | 7/1984 | Baron |
| 4,470,407 | A | 9/1984 | Hussein |
| 4,497,319 | A | 2/1985 | Sekine et al. |
| 4,501,274 | A | 2/1985 | Skjaerpe |
| 4,517,973 | A | 5/1985 | Sunago et al. |
| 4,538,608 | A | 9/1985 | L'Esperance |
| 4,548,205 | A | 10/1985 | Armeniades et al. |
| 4,551,129 | A | 11/1985 | Coleman et al. |
| 4,558,698 | A | 12/1985 | O'Dell |
| 4,559,942 | A | 12/1985 | Eisenberg |
| 4,566,438 | A | 1/1986 | Liese et al. |
| 4,580,559 | A | 4/1986 | L'Esperance |
| 4,583,539 | A | 4/1986 | Karlin et al. |
| 4,601,713 | A | 7/1986 | Fuquo |
| 4,604,087 | A | 8/1986 | Joseph |
| 4,633,866 | A | 1/1987 | Peyman et al. |
| 4,658,816 | A | 4/1987 | Ector |
| 4,660,546 | A | 4/1987 | Herrick et al. |
| 4,671,273 | A | 6/1987 | Lindsey |
| 4,689,040 | A | 8/1987 | Thompson |
| 4,699,140 | A | 10/1987 | Holmes et al. |
| 4,706,669 | A | 11/1987 | Schlegel |
| 4,722,350 | A | 2/1988 | Armeniades et al. |
| 4,722,724 | A | 2/1988 | Schocket |
| 4,729,373 | A | 3/1988 | Peyman |
| 4,733,665 | A | 3/1988 | Palmaz |
| 4,750,901 | A | 6/1988 | Molteno |
| 4,770,654 | A | 9/1988 | Rogers et al. |
| 4,791,927 | A | 12/1988 | Menger |
| 4,826,478 | A | 5/1989 | Schocket |
| 4,846,172 | A | 7/1989 | Berlin |
| 4,861,341 | A | 8/1989 | Woodburn |
| 4,876,250 | A | 10/1989 | Clark |
| 4,880,000 | A | 11/1989 | Holmes et al. |
| 4,886,488 | A | 12/1989 | White |
| 4,919,130 | A | 4/1990 | Stoy et al. |
| 4,925,299 | A | 5/1990 | Meisberger et al. |
| 4,934,363 | A | 6/1990 | Smith et al. |
| 4,934,809 | A | 6/1990 | Volk |
| 4,936,825 | A | 6/1990 | Ungerleider |
| 4,946,436 | A | 8/1990 | Smith |
| 4,968,296 | A | 11/1990 | Ritch et al. |
| 4,994,060 | A | 2/1991 | Rink et al. |
| 5,034,010 | A | 7/1991 | Kittrell et al. |
| 5,092,837 | A | 3/1992 | Ritch et al. |
| 5,123,902 | A | 6/1992 | Muller et al. |
| 5,127,901 | A | 7/1992 | Odrich |
| 5,129,895 | A | 7/1992 | Vassiliadis et al. |
| 5,178,604 | A | 1/1993 | Baerveldt et al. |
| 5,180,362 | A | 1/1993 | Worst |
| 5,190,552 | A | 3/1993 | Kelman |
| 5,213,569 | A | 5/1993 | Davis |
| 5,246,452 | A | 9/1993 | Sinnott |
| 5,254,112 | A | 10/1993 | Sinofsky et al. |
| 5,273,056 | A | 12/1993 | McLaughlin et al. |
| 5,290,267 | A | 3/1994 | Zimmermann |
| 5,300,020 | A | 4/1994 | L'Esperance |
| 5,359,685 | A | 10/1994 | Waynant et al. |
| 5,360,399 | A | 11/1994 | Stegmann |
| 5,371,078 | A | 12/1994 | Clark et al. |
| 5,372,577 | A | 12/1994 | Ungerleider |
| 5,445,637 | A | 8/1995 | Bretton |
| 5,454,796 | A | 10/1995 | Krupin |
| 5,458,615 | A | 10/1995 | Klemm et al. |
| 5,501,274 | A | 3/1996 | Nguyen et al. |
| 5,536,259 | A | 7/1996 | Utterberg |
| 5,575,780 | A | 11/1996 | Saito |
| 5,591,223 | A | 1/1997 | Lock et al. |
| 5,607,966 | A | 3/1997 | Hellberg et al. |
| 5,613,972 | A | 3/1997 | Lee et al. |
| 5,626,558 | A | 5/1997 | Suson |
| 5,643,250 | A | 7/1997 | O'Donnell |
| 5,653,753 | A | 8/1997 | Brady et al. |
| 5,657,760 | A | 8/1997 | Ying et al. |
| 5,676,669 | A | 10/1997 | Colvard |
| 5,704,907 | A | 1/1998 | Nordquist et al. |
| 5,713,844 | A | 2/1998 | Peyman |
| 5,722,970 | A | 3/1998 | Colvard et al. |
| 5,738,676 | A | 4/1998 | Hammer et al. |
| 5,738,677 | A | 4/1998 | Colvard et al. |
| 5,785,658 | A | 7/1998 | Benaron et al. |
| 5,792,099 | A | 8/1998 | DeCamp et al. |
| 5,792,103 | A | 8/1998 | Schwartz et al. |
| 5,807,302 | A | 9/1998 | Wandel |
| 5,811,453 | A | 9/1998 | Yanni et al. |
| 5,865,831 | A | 2/1999 | Cozean et al. |
| 5,868,697 | A | 2/1999 | Richter et al. |
| 5,879,319 | A | 3/1999 | Pynson et al. |
| 5,885,279 | A | 3/1999 | Bretton |
| 5,893,837 | A | 4/1999 | Eagles et al. |
| 5,895,831 | A | 4/1999 | Brasier et al. |
| 5,919,171 | A | 7/1999 | Kira et al. |
| 5,948,427 | A | 9/1999 | Yamamoto et al. |
| 5,968,058 | A | 10/1999 | Richter et al. |
| 5,984,963 | A | 11/1999 | Ryan et al. |
| 5,990,099 | A | 11/1999 | Clark |
| 5,993,438 | A | 11/1999 | Juhasz et al. |
| 5,997,531 | A | 12/1999 | Loeb et al. |
| 6,002,480 | A | 12/1999 | Izatt et al. |
| 6,007,511 | A | 12/1999 | Prywes |
| 6,050,970 | A | 4/2000 | Baerveldt |
| 6,083,193 | A | 7/2000 | Kadziauskas et al. |
| 6,099,521 | A | 8/2000 | Shadduck |
| 6,102,045 | A | 8/2000 | Nordquist et al. |
| 6,142,990 | A | 11/2000 | Burk |
| 6,146,375 | A | 11/2000 | Juhasz et al. |
| 6,177,544 | B1 | 1/2001 | Kanal et al. |
| 6,186,974 | B1 | 2/2001 | Allan et al. |
| 6,217,584 | B1 | 4/2001 | Nun |
| 6,221,078 | B1 | 4/2001 | Bylsma |
| 6,238,409 | B1 | 5/2001 | Hojeibane |
| 6,241,721 | B1 | 6/2001 | Cozean et al. |
| D444,874 | S | 7/2001 | Haffner et al. |
| 6,297,228 | B1 | 10/2001 | Clark |
| 6,319,274 | B1 | 11/2001 | Shadduck |
| 6,328,747 | B1 | 12/2001 | Nun |
| 6,375,642 | B1 | 4/2002 | Grieshaber et al. |
| 6,398,809 | B1 | 6/2002 | Hoffmann et al. |
| 6,409,752 | B1 | 6/2002 | Boatman et al. |
| 6,450,984 | B1 | 9/2002 | Lynch et al. |
| 6,464,724 | B1 | 10/2002 | Lynch et al. |
| 6,471,666 | B1 | 10/2002 | Odrich |
| 6,494,857 | B1 | 12/2002 | Neuhann |
| 6,508,779 | B1 | 1/2003 | Suson |
| 6,517,523 | B1 | 2/2003 | Kaneko et al. |
| 6,524,275 | B1 | 2/2003 | Lynch et al. |
| 6,533,764 | B1 | 3/2003 | Haffner et al. |
| 6,533,768 | B1 | 3/2003 | Hill |

(56) References Cited

U.S. PATENT DOCUMENTS 6,544,208 B2 4/2003 Ethier et al.
6,544,249 B1 4/2003 Yu et al.
6,551,289 B1 4/2003 Higuchi et al.
6,626,858 B2 9/2003 Lynch et al.
6,638,239 B1 10/2003 Bergheim et al.
6,666,841 B2 12/2003 Gharib et al.
6,699,210 B2 3/2004 Williams et al.
6,699,211 B2 3/2004 Savage
6,702,790 B1 3/2004 Ross
6,726,676 B2 4/2004 Stegmann et al.
D490,152 S 5/2004 Myall et al.
6,730,056 B1 5/2004 Ghaem et al.
6,736,791 B1 5/2004 Tu et al.
6,780,164 B2 8/2004 Bergheim et al.
6,783,544 B2 8/2004 Lynch et al.
6,827,699 B2 12/2004 Lynch et al.
6,827,700 B2 12/2004 Lynch et al.
6,881,198 B2 4/2005 Brown
6,899,717 B2 5/2005 Weber et al.
6,939,298 B2 9/2005 Brown et al.
6,955,656 B2 10/2005 Bergheim et al.
6,962,573 B1 11/2005 Wilcox
6,981,958 B1 1/2006 Gharib et al.
6,989,007 B2 1/2006 Shadduck
7,018,376 B2 3/2006 Webb et al.
7,094,225 B2 8/2006 Tu et al.
7,125,119 B2 10/2006 Farberov
7,133,137 B2 11/2006 Shimmick
7,135,009 B2 11/2006 Tu et al.
7,147,650 B2 12/2006 Lee
7,163,543 B2 1/2007 Smedley et al.
7,186,232 B1 3/2007 Smedley et al.
7,192,412 B1 3/2007 Zhou et al.
7,207,965 B2 4/2007 Simon
7,207,980 B2 4/2007 Christian et al.
7,220,238 B2 5/2007 Lynch et al.
7,273,475 B2 9/2007 Tu et al.
7,297,130 B2 11/2007 Bergheim et al.
7,331,984 B2 2/2008 Tu et al.
7,488,303 B1 2/2009 Haffner et al.
7,699,882 B2 4/2010 Stamper et al.
7,740,604 B2 6/2010 Schieber et al.
7,931,596 B2 4/2011 Rachlin et al.
7,967,772 B2 6/2011 McKenzie et al.
8,012,115 B2 9/2011 Karageozian
8,123,729 B2 2/2012 Yamamoto et al.
8,172,899 B2 5/2012 Silvestrini et al.
8,267,882 B2 9/2012 Euteneuer et al.
8,282,592 B2 10/2012 Schieber et al.
8,308,701 B2 11/2012 Horvath et al.
8,337,509 B2 12/2012 Schieber et al.
8,372,026 B2 2/2013 Schieber et al.
8,414,518 B2 4/2013 Schieber et al.
8,425,449 B2 4/2013 Wardle et al.
8,475,374 B2 7/2013 Irazoqui et al.
8,512,404 B2 8/2013 Frion et al.
8,529,494 B2 9/2013 Euteneuer et al.
8,540,659 B2 9/2013 Berlin
8,551,166 B2 10/2013 Schieber et al.
8,629,161 B2 1/2014 Mizuno et al.
8,636,647 B2 1/2014 Silvestrini et al.
8,647,659 B2 2/2014 Robinson et al.
8,657,776 B2 2/2014 Wardle et al.
8,663,150 B2 3/2014 Wardle et al.
8,663,303 B2 3/2014 Horvath et al.
8,734,377 B2 5/2014 Schieber et al.
8,808,222 B2 8/2014 Schieber et al.
8,939,906 B2 1/2015 Huang et al.
8,939,948 B2 1/2015 De Juan, Jr. et al.
8,945,038 B2 2/2015 Yablonski
8,951,221 B2 2/2015 Stegmann et al.
8,961,447 B2 2/2015 Schieber et al.
8,974,511 B2 3/2015 Horvath et al.
9,039,650 B2 5/2015 Schieber et al.
9,050,169 B2 6/2015 Schieber et al.
9,066,750 B2 6/2015 Wardle et al.
9,066,783 B2 6/2015 Euteneuer et al.
9,155,655 B2 10/2015 Schieber et al.
9,211,213 B2 12/2015 Wardle et al.
9,226,852 B2 1/2016 Schieber et al.
9,301,875 B2 4/2016 Tu et al.
9,351,874 B2 5/2016 Schieber et al.
9,358,156 B2 6/2016 Wardle et al.
9,402,767 B2 8/2016 Schieber et al.
9,510,973 B2 12/2016 Wardle
9,579,234 B2 2/2017 Wardle et al.
9,603,741 B2 3/2017 Berlin
9,610,196 B2 4/2017 Schieber et al.
9,636,254 B2 5/2017 Yu et al.
9,642,746 B2 5/2017 Berlin
9,693,899 B2 7/2017 Wardle et al.
9,693,901 B2 7/2017 Horvath et al.
9,693,902 B2 7/2017 Euteneuer et al.
9,730,638 B2 8/2017 Haffner et al.
9,757,276 B2 9/2017 Penhasi
9,775,729 B2 10/2017 McClain et al.
9,782,293 B2 10/2017 Doci
9,788,999 B2 10/2017 Schaller
9,795,503 B2 10/2017 Perez Grossmann
9,808,373 B2 11/2017 Horvath et al.
9,820,883 B2 11/2017 Berlin
9,833,357 B2 12/2017 Berlin
9,931,243 B2 4/2018 Wardle et al.
10,159,601 B2 12/2018 Berlin
10,335,314 B2 7/2019 Berlin
10,363,168 B2 7/2019 Schieber et al.
10,390,993 B1 8/2019 Berlin
10,406,025 B2 9/2019 Wardle et al.
10,492,949 B2 12/2019 Wardle et al.
10,537,474 B2 1/2020 Euteneuer et al.
10,617,558 B2 4/2020 Schieber et al.
10,687,978 B2 6/2020 Berlin
10,709,547 B2 7/2020 Schieber
11,026,836 B2 6/2021 Wardle et al.
11,135,088 B2 10/2021 Wardle et al.
11,197,779 B2 12/2021 Van Meter et al.
2001/0002438 A1 5/2001 Sepetka et al.
2001/0021835 A1 9/2001 Mitchell et al.
2002/0003546 A1 1/2002 Mochimaru et al.
2002/0013546 A1 1/2002 Grieshaber et al.
2002/0013572 A1 1/2002 Berlin
2002/0052653 A1 5/2002 Durgin
2002/0072673 A1 6/2002 Yamamoto et al.
2002/0082591 A1 6/2002 Haefliger
2002/0133168 A1 9/2002 Smedley et al.
2002/0143284 A1 10/2002 Tu et al.
2002/0165504 A1 11/2002 Sharp et al.
2002/0165522 A1 11/2002 Holmen
2002/0193805 A1 12/2002 Ott et al.
2003/0004457 A1 1/2003 Andersson
2003/0014092 A1 1/2003 Neuhann
2003/0040754 A1 2/2003 Mitchell et al.
2003/0055372 A1 3/2003 Lynch et al.
2003/0060748 A1 3/2003 Baikoff
2003/0060752 A1 3/2003 Bergheim et al.
2003/0060784 A1 3/2003 Hilgers et al.
2003/0093084 A1 5/2003 Nissan et al.
2003/0097151 A1 5/2003 Smedley et al.
2003/0105456 A1 6/2003 Lin
2003/0125351 A1 7/2003 Azuma et al.
2003/0175324 A1 9/2003 Robinson et al.
2003/0181848 A1 9/2003 Bergheim et al.
2003/0187384 A1 10/2003 Bergheim et al.
2003/0212387 A1 11/2003 Kurtz et al.
2003/0229303 A1 12/2003 Haffner et al.
2003/0236483 A1 12/2003 Ren
2003/0236484 A1 12/2003 Lynch et al.
2004/0024345 A1 2/2004 Gharib et al.
2004/0024453 A1 2/2004 Castillejos
2004/0030302 A1 2/2004 Kamata et al.
2004/0070761 A1 4/2004 Horvath et al.
2004/0082939 A1 4/2004 Berlin
2004/0088048 A1 5/2004 Richter et al.
2004/0092856 A1 5/2004 Dahan

(56) References Cited

U.S. PATENT DOCUMENTS

| | | | |
|---|---|---|---|
| 2004/0098124 | A1 | 5/2004 | Freeman et al. |
| 2004/0102729 | A1 | 5/2004 | Haffner et al. |
| 2004/0106975 | A1 | 6/2004 | Solovay et al. |
| 2004/0111050 | A1 | 6/2004 | Smedley et al. |
| 2004/0116909 | A1 | 6/2004 | Neuberger et al. |
| 2004/0122380 | A1 | 6/2004 | Utterberg |
| 2004/0127843 | A1 | 7/2004 | Tu et al. |
| 2004/0147870 | A1 | 7/2004 | Burns et al. |
| 2004/0193095 | A1 | 9/2004 | Shadduck |
| 2004/0193262 | A1 | 9/2004 | Shadduck |
| 2004/0199149 | A1 | 10/2004 | Myers et al. |
| 2004/0199171 | A1 | 10/2004 | Akahoshi |
| 2004/0210181 | A1 | 10/2004 | Vass et al. |
| 2004/0210185 | A1 | 10/2004 | Tu et al. |
| 2004/0216749 | A1 | 11/2004 | Tu |
| 2004/0225357 | A1 | 11/2004 | Worst et al. |
| 2004/0228013 | A1 | 11/2004 | Goldstein et al. |
| 2004/0249333 | A1 | 12/2004 | Bergheim et al. |
| 2004/0254517 | A1 | 12/2004 | Quiroz-Mercado et al. |
| 2004/0254519 | A1 | 12/2004 | Tu et al. |
| 2004/0254520 | A1 | 12/2004 | Porteous et al. |
| 2004/0260228 | A1 | 12/2004 | Lynch et al. |
| 2005/0041200 | A1 | 2/2005 | Rich |
| 2005/0043722 | A1 | 2/2005 | Lin |
| 2005/0049578 | A1 | 3/2005 | Tu et al. |
| 2005/0090806 | A1 | 4/2005 | Lynch et al. |
| 2005/0090807 | A1 | 4/2005 | Lynch et al. |
| 2005/0101967 | A1 | 5/2005 | Weber et al. |
| 2005/0107734 | A1 | 5/2005 | Coroneo |
| 2005/0119601 | A9 | 6/2005 | Lynch et al. |
| 2005/0119636 | A1 | 6/2005 | Haffner et al. |
| 2005/0125003 | A1 | 6/2005 | Pinchuk et al. |
| 2005/0131514 | A1 | 6/2005 | Hijlkema et al. |
| 2005/0149114 | A1 | 7/2005 | Cartledge et al. |
| 2005/0154443 | A1 | 7/2005 | Linder et al. |
| 2005/0165385 | A1 | 7/2005 | Simon |
| 2005/0192527 | A1 | 9/2005 | Gharib et al. |
| 2005/0197667 | A1 | 9/2005 | Chan et al. |
| 2005/0203542 | A1 | 9/2005 | Weber et al. |
| 2005/0209549 | A1 | 9/2005 | Bergheim et al. |
| 2005/0209550 | A1 | 9/2005 | Bergheim et al. |
| 2005/0240168 | A1 | 10/2005 | Neuberger et al. |
| 2005/0244464 | A1 | 11/2005 | Hughes |
| 2005/0245916 | A1 | 11/2005 | Connor |
| 2005/0250788 | A1 | 11/2005 | Tu et al. |
| 2005/0260186 | A1 | 11/2005 | Bookbinder et al. |
| 2005/0266047 | A1 | 12/2005 | Tu et al. |
| 2005/0271704 | A1 | 12/2005 | Tu et al. |
| 2005/0273033 | A1 | 12/2005 | Grahn et al. |
| 2005/0277864 | A1 | 12/2005 | Haffner et al. |
| 2005/0279369 | A1 | 12/2005 | Lin |
| 2005/0288619 | A1 | 12/2005 | Gharib et al. |
| 2005/0288745 | A1 | 12/2005 | Andersen et al. |
| 2006/0020247 | A1 | 1/2006 | Kagan et al. |
| 2006/0021623 | A1 | 2/2006 | Miller et al. |
| 2006/0032507 | A1 | 2/2006 | Tu |
| 2006/0052879 | A1 | 3/2006 | Kolb |
| 2006/0069340 | A1 | 3/2006 | Simon |
| 2006/0074375 | A1 | 4/2006 | Bergheim et al. |
| 2006/0079828 | A1 | 4/2006 | Brown |
| 2006/0084907 | A1 | 4/2006 | Bergheim et al. |
| 2006/0084954 | A1 | 4/2006 | Zadoyan et al. |
| 2006/0106370 | A1 | 5/2006 | Baerveldt et al. |
| 2006/0110428 | A1 | 5/2006 | deJuan et al. |
| 2006/0116626 | A1 | 6/2006 | Smedley et al. |
| 2006/0129141 | A1 | 6/2006 | Lin |
| 2006/0149194 | A1 | 7/2006 | Conston et al. |
| 2006/0154981 | A1 | 7/2006 | Klimko et al. |
| 2006/0155238 | A1 | 7/2006 | Shields |
| 2006/0155265 | A1 | 7/2006 | Juhasz et al. |
| 2006/0155300 | A1 | 7/2006 | Stamper et al. |
| 2006/0167421 | A1 | 7/2006 | Quinn |
| 2006/0167466 | A1 | 7/2006 | Dusek |
| 2006/0173397 | A1 | 8/2006 | Tu et al. |
| 2006/0173399 | A1 | 8/2006 | Rodgers et al. |
| 2006/0178674 | A1 | 8/2006 | McIntyre |
| 2006/0189915 | A1 | 8/2006 | Camras et al. |
| 2006/0189916 | A1 | 8/2006 | Bas et al. |
| 2006/0189917 | A1 | 8/2006 | Mayr et al. |
| 2006/0195055 | A1 | 8/2006 | Bergheim et al. |
| 2006/0195056 | A1 | 8/2006 | Bergheim et al. |
| 2006/0195187 | A1 | 8/2006 | Stegmann et al. |
| 2006/0200113 | A1 | 9/2006 | Haffner et al. |
| 2006/0224146 | A1 | 10/2006 | Lin |
| 2006/0241749 | A1 | 10/2006 | Tu et al. |
| 2006/0259021 | A1 | 11/2006 | Lin |
| 2006/0264971 | A1 | 11/2006 | Akahoshi |
| 2006/0276759 | A1 | 12/2006 | Kinast et al. |
| 2007/0010827 | A1 | 1/2007 | Tu et al. |
| 2007/0021725 | A1 | 1/2007 | Villette |
| 2007/0027452 | A1 | 2/2007 | Varner et al. |
| 2007/0073275 | A1 | 3/2007 | Conston et al. |
| 2007/0088432 | A1 | 4/2007 | Solovay et al. |
| 2007/0093794 | A1 | 4/2007 | Wang et al. |
| 2007/0093796 | A1 | 4/2007 | Raksi et al. |
| 2007/0106200 | A1 | 5/2007 | Levy |
| 2007/0106236 | A1 | 5/2007 | Coroneo |
| 2007/0112292 | A1 | 5/2007 | Tu et al. |
| 2007/0118147 | A1 | 5/2007 | Smedley et al. |
| 2007/0121120 | A1 | 5/2007 | Schachar |
| 2007/0135681 | A1 | 6/2007 | Chin et al. |
| 2007/0173791 | A1 | 7/2007 | Raksi |
| 2007/0179520 | A1 | 8/2007 | West |
| 2007/0191863 | A1 | 8/2007 | De Juan, Jr. et al. |
| 2007/0202186 | A1 | 8/2007 | Yamamoto et al. |
| 2007/0208325 | A1 | 9/2007 | Kurtz |
| 2007/0219509 | A1 | 9/2007 | Tashiro et al. |
| 2007/0219541 | A1 | 9/2007 | Kurtz |
| 2007/0235543 | A1 | 10/2007 | Zadoyan et al. |
| 2007/0236771 | A1 | 10/2007 | Zadoyan et al. |
| 2007/0265582 | A1 | 11/2007 | Kaplan et al. |
| 2007/0270945 | A1 | 11/2007 | Kobayashi et al. |
| 2007/0276315 | A1 | 11/2007 | Haffner et al. |
| 2007/0276316 | A1 | 11/2007 | Haffner et al. |
| 2007/0282244 | A1 | 12/2007 | Tu et al. |
| 2007/0282245 | A1 | 12/2007 | Tu et al. |
| 2007/0293807 | A1 | 12/2007 | Lynch et al. |
| 2007/0293872 | A1 | 12/2007 | Peyman |
| 2007/0298068 | A1 | 12/2007 | Badawi et al. |
| 2008/0015488 | A1 | 1/2008 | Tu et al. |
| 2008/0027519 | A1 | 1/2008 | Guerrero |
| 2008/0045878 | A1 | 2/2008 | Bergheim et al. |
| 2008/0058704 | A1 | 3/2008 | Hee et al. |
| 2008/0058777 | A1 | 3/2008 | Kurtz et al. |
| 2008/0082088 | A1 | 4/2008 | Kurtz et al. |
| 2008/0091224 | A1 | 4/2008 | Griffis et al. |
| 2008/0119827 | A1 | 5/2008 | Kurtz et al. |
| 2008/0228127 | A1 | 9/2008 | Burns et al. |
| 2008/0278687 | A1 | 11/2008 | Somani |
| 2008/0288082 | A1 | 11/2008 | Deal |
| 2008/0312661 | A1 | 12/2008 | Downer et al. |
| 2009/0005852 | A1 | 1/2009 | Gittings et al. |
| 2009/0028953 | A1 | 1/2009 | Yamamoto et al. |
| 2009/0030363 | A1 | 1/2009 | Gellman |
| 2009/0030381 | A1 | 1/2009 | Lind et al. |
| 2009/0036843 | A1 | 2/2009 | Erskine |
| 2009/0043321 | A1 | 2/2009 | Conston et al. |
| 2009/0054723 | A1 | 2/2009 | Khairkhahan et al. |
| 2009/0069786 | A1 | 3/2009 | Vesely et al. |
| 2009/0082862 | A1 | 3/2009 | Schieber et al. |
| 2009/0104248 | A1 | 4/2009 | Rapacki et al. |
| 2009/0118716 | A1 | 5/2009 | Brownell |
| 2009/0118717 | A1 | 5/2009 | Brownell et al. |
| 2009/0118718 | A1 | 5/2009 | Raksi et al. |
| 2009/0131921 | A1 | 5/2009 | Kurtz et al. |
| 2009/0137988 | A1 | 5/2009 | Kurtz |
| 2009/0138081 | A1 | 5/2009 | Bergheim et al. |
| 2009/0157062 | A1 | 6/2009 | Hauger et al. |
| 2009/0171327 | A1 | 7/2009 | Kurtz et al. |
| 2009/0182421 | A1 | 7/2009 | Silvestrini et al. |
| 2009/0198248 | A1 | 8/2009 | Yeung et al. |
| 2009/0204053 | A1 | 8/2009 | Nissan et al. |
| 2009/0247955 | A1 | 10/2009 | Yamamoto et al. |
| 2009/0259126 | A1 | 10/2009 | Saal et al. |

(56) References Cited

U.S. PATENT DOCUMENTS

| | | | |
|---|---|---|---|
| 2009/0281520 A1 | 11/2009 | Highley et al. | |
| 2009/0281530 A1 | 11/2009 | Korn | |
| 2009/0291423 A1 | 11/2009 | Hara | |
| 2010/0004580 A1 | 1/2010 | Lynch et al. | |
| 2010/0036488 A1 | 2/2010 | de Juan et al. | |
| 2010/0057072 A1 | 3/2010 | Roman et al. | |
| 2010/0114309 A1 | 5/2010 | de Juan et al. | |
| 2010/0137981 A1 | 6/2010 | Silvestrini et al. | |
| 2010/0173866 A1 | 7/2010 | Hee et al. | |
| 2010/0191176 A1 | 7/2010 | Ho et al. | |
| 2010/0191177 A1 | 7/2010 | Chang et al. | |
| 2010/0234726 A1 | 9/2010 | Sirimanne et al. | |
| 2010/0234790 A1 | 9/2010 | Tu et al. | |
| 2010/0262174 A1 | 10/2010 | Sretavan et al. | |
| 2010/0324543 A1 | 12/2010 | Kurtz et al. | |
| 2010/0331858 A1 | 12/2010 | Simaan et al. | |
| 2011/0028948 A1 | 2/2011 | Raksi et al. | |
| 2011/0028949 A1 | 2/2011 | Raksi et al. | |
| 2011/0028950 A1 | 2/2011 | Raksi et al. | |
| 2011/0028951 A1 | 2/2011 | Raksi et al. | |
| 2011/0028952 A1 | 2/2011 | Raksi et al. | |
| 2011/0028953 A1 | 2/2011 | Raksi et al. | |
| 2011/0028954 A1 | 2/2011 | Raksi et al. | |
| 2011/0028955 A1 | 2/2011 | Raksi | |
| 2011/0028957 A1 | 2/2011 | Raksi et al. | |
| 2011/0028958 A1 | 2/2011 | Raksi et al. | |
| 2011/0098809 A1 | 4/2011 | Wardle et al. | |
| 2011/0196487 A1 | 8/2011 | Badawi et al. | |
| 2011/0218523 A1 | 9/2011 | Robl | |
| 2011/0224597 A1 | 9/2011 | Stegmann et al. | |
| 2012/0010702 A1 | 1/2012 | Stegmann et al. | |
| 2012/0021397 A1 | 1/2012 | Van Dalen et al. | |
| 2012/0022424 A1 | 1/2012 | Yamamoto et al. | |
| 2012/0035524 A1 | 2/2012 | Silvestrini | |
| 2012/0191064 A1 | 7/2012 | Conston et al. | |
| 2012/0271272 A1 | 10/2012 | Hammack et al. | |
| 2012/0283557 A1 | 11/2012 | Berlin | |
| 2012/0302861 A1 | 11/2012 | Marshall et al. | |
| 2013/0023837 A1 | 1/2013 | Becker | |
| 2013/0182223 A1 | 7/2013 | Wardle et al. | |
| 2013/0184631 A1 | 7/2013 | Pinchuk | |
| 2013/0253402 A1 | 9/2013 | Badawi et al. | |
| 2013/0253403 A1 | 9/2013 | Badawi et al. | |
| 2013/0253437 A1 | 9/2013 | Badawi et al. | |
| 2013/0253438 A1 | 9/2013 | Badawi et al. | |
| 2013/0253528 A1 | 9/2013 | Haffner et al. | |
| 2013/0267887 A1 | 10/2013 | Kahook et al. | |
| 2013/0281908 A1 | 10/2013 | Schaller et al. | |
| 2014/0018720 A1 | 1/2014 | Horvath et al. | |
| 2014/0066821 A1 | 3/2014 | Freidland et al. | |
| 2014/0066831 A1 | 3/2014 | Silvestrini et al. | |
| 2014/0081195 A1 | 3/2014 | Clauson et al. | |
| 2015/0018746 A1 | 1/2015 | Hattenbach | |
| 2015/0022780 A1 | 1/2015 | John et al. | |
| 2015/0038893 A1 | 2/2015 | Haffner et al. | |
| 2015/0045714 A1 | 2/2015 | Horvath et al. | |
| 2015/0057583 A1 | 2/2015 | Gunn et al. | |
| 2015/0057591 A1 | 2/2015 | Horvath et al. | |
| 2015/0065940 A1 | 3/2015 | Rangel-Friedman et al. | |
| 2015/0148836 A1 | 5/2015 | Heeren | |
| 2015/0305939 A1 | 10/2015 | Vera et al. | |
| 2015/0305940 A1 | 10/2015 | Vera et al. | |
| 2015/0313759 A1 | 11/2015 | Vera et al. | |
| 2016/0063898 A1 | 3/2016 | Bernal | |
| 2017/0127941 A1 | 5/2017 | Ostermeier et al. | |
| 2017/0143541 A1 | 5/2017 | Badawi et al. | |
| 2017/0164831 A1 | 6/2017 | Choo et al. | |
| 2017/0172794 A1 | 6/2017 | Varner et al. | |
| 2017/0172795 A1 | 6/2017 | Lerner | |
| 2017/0172797 A1 | 6/2017 | Horvath et al. | |
| 2017/0172798 A1 | 6/2017 | Horvath et al. | |
| 2017/0172799 A1 | 6/2017 | Horvath | |
| 2017/0172800 A1 | 6/2017 | Romoda et al. | |
| 2017/0202708 A1 | 7/2017 | Berlin | |
| 2017/0239272 A1 | 8/2017 | Ambati et al. | |
| 2017/0251921 A1 | 9/2017 | Phan et al. | |
| 2017/0280997 A1 | 10/2017 | Lai et al. | |
| 2017/0281409 A1 | 10/2017 | Haffner et al. | |
| 2017/0348150 A1 | 12/2017 | Horvath et al. | |
| 2017/0360609 A9 | 12/2017 | Schieber et al. | |
| 2018/0360655 A1 | 12/2018 | Berlin | |
| 2018/0369017 A1 | 12/2018 | Schieber et al. | |
| 2019/0343679 A1 | 11/2019 | Wardle et al. | |
| 2019/0380874 A1 | 12/2019 | Schieber et al. | |
| 2020/0060876 A1 | 2/2020 | Wardle et al. | |
| 2020/0085620 A1 | 3/2020 | Euteneuer | |
| 2020/0118466 A1 * | 4/2020 | Bernal | G09B 23/32 |
| 2020/0135056 A1 * | 4/2020 | Omata | G09B 23/28 |
| 2020/0197221 A1 | 6/2020 | Schieber et al. | |
| 2020/0222238 A1 | 7/2020 | Schieber et al. | |
| 2020/0261270 A1 | 8/2020 | Berlin | |
| 2021/0030590 A1 | 2/2021 | Blanda et al. | |
| 2021/0330499 A1 | 10/2021 | Wardle et al. | |
| 2021/0361479 A1 | 11/2021 | Wardle et al. | |
| 2022/0054314 A1 | 2/2022 | Van Meter et al. | |
| 2022/0096271 A1 | 3/2022 | Wardle et al. | |
| 2023/0237932 A1 * | 7/2023 | Slabber | G09B 23/30<br>434/271 |

FOREIGN PATENT DOCUMENTS

| | | |
|---|---|---|
| DE | 102012221350 A1 | 5/2014 |
| EP | 0168201 B1 | 6/1988 |
| EP | 0957949 A1 | 11/1996 |
| EP | 0766544 B1 | 5/1998 |
| EP | 1615604 B1 | 8/2009 |
| EP | 2193821 A1 | 6/2010 |
| EP | 1715827 B1 | 12/2010 |
| EP | 2380622 A1 | 10/2011 |
| EP | 2468327 A1 | 6/2012 |
| EP | 2471563 A1 | 7/2012 |
| EP | 1833440 B1 | 8/2012 |
| EP | 3164061 A1 | 5/2017 |
| EP | 2996648 B1 | 6/2017 |
| EP | 1732484 B1 | 8/2017 |
| EP | 1740153 B2 | 8/2017 |
| EP | 3076948 A4 | 8/2017 |
| EP | 3205333 A1 | 8/2017 |
| EP | 3060180 A4 | 9/2017 |
| EP | 3082570 A4 | 9/2017 |
| JP | 10504978 A | 5/1998 |
| JP | 11123205 A | 5/1999 |
| JP | 2002542872 A | 12/2002 |
| JP | 2006517848 A | 8/2006 |
| JP | 2006289075 A | 10/2006 |
| JP | 2009523545 A | 6/2009 |
| JP | 2010509003 A | 3/2010 |
| JP | 2011502649 A | 1/2011 |
| JP | 2012527318 A | 11/2012 |
| JP | 2015517836 A | 6/2015 |
| JP | 2017517363 A | 6/2017 |
| WO | WO96/20742 A1 | 7/1996 |
| WO | WO99/01063 A1 | 1/1999 |
| WO | WO99/45868 A1 | 9/1999 |
| WO | WO00/07525 A1 | 2/2000 |
| WO | WO00/64389 A1 | 11/2000 |
| WO | WO00/64393 A1 | 11/2000 |
| WO | WO00/67687 A1 | 11/2000 |
| WO | WO01/89437 A2 | 11/2001 |
| WO | WO01/97727 A1 | 12/2001 |
| WO | WO02/36052 A1 | 5/2002 |
| WO | WO02/074052 A2 | 9/2002 |
| WO | WO02/080811 A2 | 10/2002 |
| WO | WO03/015659 A2 | 2/2003 |
| WO | WO03/045290 A1 | 6/2003 |
| WO | WO2004/054643 A1 | 7/2004 |
| WO | WO2004/093761 A1 | 11/2004 |
| WO | WO2005/105197 A2 | 11/2005 |
| WO | WO2006/066103 A2 | 6/2006 |
| WO | WO2007/035356 A2 | 3/2007 |
| WO | WO2007/047744 A2 | 4/2007 |
| WO | WO2007/087061 A2 | 8/2007 |
| WO | WO2008/002377 A1 | 1/2008 |
| WO | WO2008/005873 A2 | 1/2008 |

(56) References Cited

FOREIGN PATENT DOCUMENTS

| | | | |
|---|---|---|---|
| WO | WO2009/120960 | A2 | 10/2009 |
| WO | WO2011/053512 | A1 | 5/2011 |
| WO | WO2011/057283 | A1 | 5/2011 |
| WO | WO2011/106781 | A1 | 9/2011 |
| WO | WO2011/150045 | A1 | 12/2011 |
| WO | WO2012/051575 | A2 | 4/2012 |
| WO | WO2012/083143 | A1 | 6/2012 |
| WO | WO2013/147978 | A2 | 10/2013 |
| WO | WO2016/154066 | A2 | 9/2016 |
| WO | WO2017/030902 | A2 | 2/2017 |
| WO | WO2017/030917 | A1 | 2/2017 |
| WO | WO2017/062347 | A1 | 4/2017 |
| WO | WO2017/087713 | A1 | 5/2017 |
| WO | WO2017/095825 | A1 | 6/2017 |
| WO | WO2017/132418 | A1 | 8/2017 |
| WO | WO2017/132647 | A1 | 8/2017 |
| WO | WO2017/156530 | A1 | 9/2017 |
| WO | WO2019/106803 | A1 | 6/2019 |
| WO | WO2021/055751 | A1 | 3/2021 |

OTHER PUBLICATIONS

Cambridge Dictionary; Sensor (definition); 2 pages; retrived from the internet (http://dictionary.cambridge.org/define.asp?dict=CALD &key=71811 >) on Aug. 14, 2018.

Camras et al.; A novel schlemm's canal scaffold increases outflow facility in a human anterior segment perfusion model; Invest. Opthalmol. Vis. Sci. ; 53(10); pp. 6115-6121; Sep. 1, 2012.

D'Ermo, et al.; Our results with the operation of ab externo trabeculotomy; Ophthalmologica; vol. 163; pp. 347-355; Feb. 1971.

Dietlein et al.; Morphological variability of the trabecular meshwork in glaucoma patients: implications for non-perforating glaucoma surgery: British Journal of Ophthalmology; 84(12); pp. 1354-1359; Dec. 2000.

Ellingsen et al.; Trabeculotomy and sinusotomy in enucleated human eyes; Investigative Ophthalmology; vol. 11; pp. 21-28; Jan. 1972.

Gallab et al.; Development of a spherical model with a 3D microchannel: An application to glaucoma surgery; Micromachines; 10(5):297; pp. 1-12; May 1, 2019.

Grant; Experimental aqueous perfusion in enucleated human eyes; Archives of Ophthalmology; vol. 69; pp. 783-801; Jun. 1963.

Gulati et al; A novel 8-mm schlemm's canal scaffold reduces outflow resistance in a human anterior segment perfusion model; Invest. Ophthalmol. Vis. Sci.; 54(3); pp. 1698-1704; Mar. 5, 2013.

Hays et al.; Improvement in outflow facility by two novel microinvasive glaucoma surgery implants; Invest. Ophthalmol. Vis. Sci.; 55(3); pp. 1893-1900; Mar. 1, 2014.

Huang et al.; Optical coherence tomography; Science; 254(5035); pp. 1178-1181; 12 pages (Author Manuscript); Nov. 1991.

Johnstone et al.; "Microsurgery of Schlemm's Canal and the Human Aqueous Outflow System;" American Journal of Ophthalmology, vol. 76 (6): 906-917; Dec. 1973.

Johnstone et al.; Effects of a schlemm canal scaffold on collector channel ostia in human anterior segments; Exp. Eye. Res.; 119; pp. 70-76; Feb. 2014.

Johnstone; Aqueous humor outflow system overview; Becker-Shaffer's Diagnosis and Therapy of the Glaucomas; Part 2 Aqueous Humor Dynamics; Chapter 3; pp. 25-46; Mosby Elseveir; 2009 (the year of publication is sufficiently earlier than the effective U.S. filling date and any foreign priority date so that the particular month of publication is not in issue).

Kirkness et al.; The Use of Silicone Drainage Tubing to Control Post-Keratoplasty Glaucoma; Eye; 2 (pt 5); pp. 583-590; Apr. 1988.

Lee et al.; Aqueous-venous shunt and intraocular pressure. Preliminary report of animal studies; Investigative Ophthalmology; vol. 5; No. 1; pp. 59-64; Feb. 1966.

Lee et al.; Short-pulsed neodymium-YAG laser trabeculotomy. An in vivo morphological study in the human eye; Investigative Ophthalmology and Visual Science; 29(11); pp. 1698-1707; Nov. 1988.

Lynch, Mary G.; U.S. Appl. No. 60/131,030 entitled "Devices and methods for treating glaucoma by enhancing aqueous outflow through schlemm's canal and anterior chamber angle," filed Apr. 26, 1999.

Macmilla Online Dictionary; Detector (definition); Macmilla On Line Dictionary; 2 pages; retrived from the internet (https://www.macmillandictionary.com/dictionary/british/detector) on Aug. 14, 2018.

Mãepea et al.; The pressures in the episcleral veins, schlemm's canal and the trabecular meshwork in monkeys: effects of changes in intraocular pressure; Exp. Eye Res.; vol. 49; pp. 645-663; Oct. 1989.

Molteno et al.; Long Tube Implants in the Management of Glaucoma; SA Medical Journal; 26; pp. 1062-1066; Jun. 1976.

Molteno; New implant for drainage in glaucoma; Brit. J. Ophthal; 53; pp. 606-615; Sep. 1969.

Moses, Robert; The effect of intraocular pressure on resistance to outflow; Survey of Ophthalmology; vol. 22; No. 2; pp. 88-100; Sep.-Oct. 1977.

Nakamura et al.; Femtosecond laser photodisruption of primate trabecular meshwork: an ex vivo study; Investigative Ophthalmology and Visual Science; 50(3); pp. 1198-1204; Mar. 2009.

Owen; A moving-mirror gonioscope for retinal surgery; British Journal of Ophthalmology; 61(3); pp. 246-247; Mar. 1977.

Oxford Dictionaries; Detector (definition); 1 page; retrieved from the internet (https://en.oxforddictionaries.com/definition/detector) on Aug. 14, 2018.

Oxford Dictionaries; Sensor (definition); 1 page; retrieved from te internet (http://www.askoxford.com/concise_oed/sensor?view=uk>) on Aug. 14, 2018.

Radhakrishnan et al.; Real-time optical coherence tomography of the anterior segment at 1310 nm; Archives of Opthhalmology: 119(8); pp. 1179-1185; Aug. 2001.

Rosenquist et al.; Outflow resistance of enucleated human eyes at two different perfusion pressures and different extents of trabeculotomy; Current Eye Res.; vol. 8; No. 12; pp. 1233-1240; Dec. 1989.

Savage, James; Gonioscopy in the management of glaucoma; Am. Academy of Ophthalmology; Focal Points; vol. XXIV; No. 3; pp. 1-14; Mar. 2006.

Schocket et al.; Anterior Chamber Tube Shunt to an Encircling Band in the Treatment of Neovascular Glaucoma and other Refractory Glaucomas; Ophthalmology; 92; pp. 553-562; Apr. 1985.

Schultz, Jared; Canaloplasty procedure shows promise for open-angle glaucoma in European study; Ocular Surgery News; vol. 34; Mar. 1, 2007.

Smit et al.; Effects of viscoelastic injection into schlemm's canal in primate and human eyes; J. Am. Academy of Ophthalmology; vol. 109; No. 4; pp. 786-792; Apr. 2002.

Spiegel et al.; Schlemm's canal implant: a new method to lower intraocular pressure in patients with POAG?; Ophthalmic Surgery and Lasers; vol. 30; No. 6; pp. 492-494; Jun. 1999.

Sugiyama et al.; Micro-Diaphragm Pressure Sensor; 1986 International Electron Devices Meeting; pp. 184-187; Dec. 7, 1986.

Toyran et al.; Femtosecond laser photodisruption of human trabecular meshwork: an in vitro study; Experimental Eye Research; 81(3); pp. 298-305; Sep. 2005.

Wilcox et al.; Hypothesis for Improving Accessory Filtration by Using Geometry; Journal of Glaucoma; 3; pp. 244-247; Fall 1994.

Yuan et al.; Mathematical modeling of outflow facility increase with trabecular meshwork bypass and schlemm canal dilation; J. Glaucoma; 10 pgs.; Mar. 24, 2015 (Epub ahead of print).

Noda et al.; U.S. Appl. No. 17/572,064 entitled "Systems and methods for viscoelastic delivery," filed Jan. 10, 2022.

* cited by examiner

SYNTHETIC EYE MODEL FOR OCULAR IMPLANT SURGICAL TRAINING

CROSS REFERENCE TO RELATED APPLICATIONS

This application claims the benefit of priority of U.S. Provisional Application No. 62/902,274, filed Sep. 18, 2019, which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present disclosure pertains generally, but not by way of limitation, synthetic eyes for surgical training. More particularly, the present disclosure relates to a realistic synthetic eye that can replicate the visual and tactile feedback of real surgery. Specifically the synthetic eye is designed for training/practice of inserting an implantable device for the treatment of glaucoma.

BACKGROUND

According to a draft report by The National Eye Institute (NEI) at The United States National Institutes of Health (NIH), glaucoma is now the leading cause of irreversible blindness worldwide and the second leading cause of blindness, behind cataract, in the world. Thus, the NEI draft report concludes, "it is critical that significant emphasis and resources continue to be devoted to determining the pathophysiology and management of this disease." Glaucoma researchers have found a strong correlation between high intraocular pressure and glaucoma. For this reason, eye care professionals routinely screen patients for glaucoma by measuring intraocular pressure using a device known as a tonometer. Many modern tonometers make this measurement by blowing a sudden puff of air against the outer surface of the eye.

The eye can be conceptualized as a ball filled with fluid. There are two types of fluid inside the eye. The cavity behind the lens is filled with a viscous fluid known as vitreous humor. The cavities in front of the lens are filled with a fluid know as aqueous humor. Whenever a person views an object, he or she is viewing that object through both the vitreous humor and the aqueous humor.

Whenever a person views an object, he or she is also viewing that object through the cornea and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the anterior chamber of the eye through the trabecular meshwork and into Schlemm's canal as new aqueous humor is secreted by the epithelial cells of the ciliary body. This excess aqueous humor enters the venous blood stream from Schlemm's canal and is carried along with the venous blood leaving the eye.

When the natural drainage mechanisms of the eye stop functioning properly, the pressure inside the eye begins to rise. Researchers have theorized prolonged exposure to high intraocular pressure causes damage to the optic nerve that transmits sensory information from the eye to the brain. This damage to the optic nerve results in loss of peripheral vision. As glaucoma progresses, more and more of the visual field is lost until the patient is completely blind.

Ocular stents, scaffolds, or support structures can be implanted into Schlemm's canal for the purpose of lowering intraocular pressure by facilitating the flow of aqueous humor from the anterior chamber into Schlemm's canal. These ocular implants are typically delivered into Schlemm's canal by inserting a cannula of a delivery system into the anterior chamber of the eye, through the trabecular meshwork, and advancing the implant through the cannula into Schlemm's canal. Upon implantation, the device provides a support structure, serving to dilate and restore the natural aqueous outflow pathway through Schlemm's canal, leading to a reduction of intraocular pressure.

Surgical training for delivery of ocular implants typically requires the use of human cadaver anterior segments. Prospective surgeons can practice delivery of ocular implants through the trabecular meshwork and into Schlemm's canal of eye bank eyes during the wet-lab portion of the training. However, human anterior segments are not easy to obtain, and are costly and difficult to transport and dispose of. Currently existing eye models do not properly replicate the feel and look of a human trabecular meshwork.

SUMMARY

A synthetic eye model is provided, comprising a rigid or semi-rigid eye shell, a synthetic iris base positioned within the eye shell, an eye core positioned within the eye shell and encircling the synthetic iris base, the eye core including a channel integral to the eye core configured to replicate Schlemm's canal of a human eye, and a synthetic trabecular meshwork tissue coupled to the eye shell and extending across the channel.

In some embodiments, the synthetic eye further comprises a synthetic cornea disposed over the eye shell.

In one example, the eye core further includes a protrusion adjacent to the channel and being configured to replicate a scleral spur of a human eye. In some implementations, the synthetic trabecular meshwork tissue extends across the protrusion and the channel.

In one embodiment, the synthetic trabecular meshwork comprises a hydrogel-based synthetic tissue.

In other embodiments, the rigid or semi-rigid eye shell includes a corneal portion and a scleral portion.

In some examples, the corneal portion integral to the scleral portion.

In one implementation, the eye core comprises a plurality of eye core pieces.

In another example, the synthetic eye includes one or more internal supports configured to attach to the synthetic trabecular meshwork tissue to prevent the synthetic trabecular meshwork tissue from collapsing into the channel.

In some embodiments, the synthetic eye further comprises a chamber positioned between the eye shell and the synthetic trabecular meshwork tissue.

A method performing surgical training is provided, comprising the steps of inserting an ocular implant into a synthetic eye, the ocular implant comprising an inlet portion at a proximal end and a Schlemm's canal portion disposed distal to the inlet portion, advancing the Schlemm's canal portion of the implant through a synthetic trabecular meshwork tissue, advancing the Schlemm's canal portion of the implant into a channel of the synthetic eye, so that the Schlemm's canal portion tracks the channel as it is advanced, and disposing the inlet portion of the implant in a chamber of the synthetic eye adjacent to the synthetic trabecular meshwork tissue.

A method of deploying an ocular implant into a synthetic eye is provided, comprising piercing a synthetic trabecular meshwork with a distal tip of a delivery tool from within a chamber of the synthetic eye, inserting the distal tip of the delivery tool into a channel of the synthetic eye, and advancing an ocular implant from the delivery tool to place a body portion of the ocular implant in the channel and an inlet portion of the ocular implant in the chamber.

BRIEF DESCRIPTION OF THE DRAWINGS

The disclosure may be more completely understood in consideration of the following detailed description of various embodiments in connection with the accompanying drawings, in which.

Figure 1:
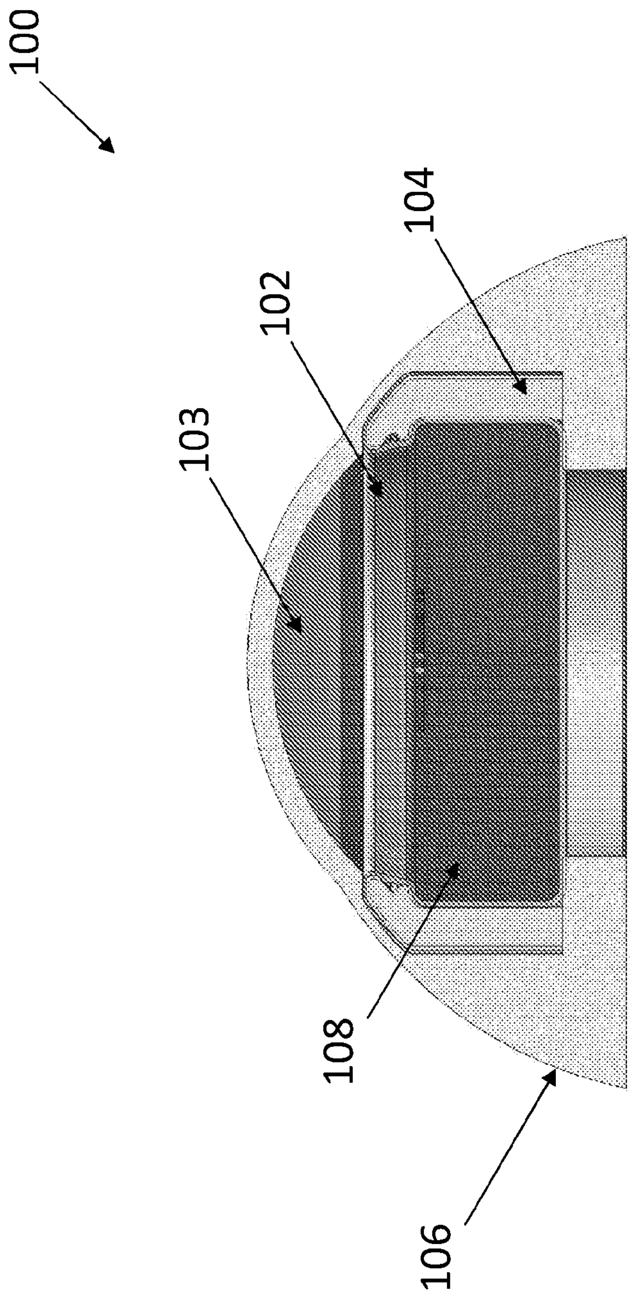
FIG. 1 illustrates one embodiment of synthetic eye model.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

The following detailed description should be read with reference to the drawings, in which similar elements in different drawings are identified with the same reference numbers. The drawings, which are not necessarily to scale, depict illustrative embodiments and are not intended to limit the scope of the disclosure.

The challenge with designing a synthetic model of the eye is producing a synthetic trabecular meshwork that properly replicates the feel and look of a human trabecular meshwork. The human trabecular meshwork is a thin delicate structure with membrane like properties. It is fragile and thin, but also stretchy and resilient. The appearance of the trabecular meshwork can vary with pigment amount and location within the angle.

According to the present disclosure, a synthetic eye model includes several design elements. Referring to FIG. 1, a synthetic eye model 100 can include a synthetic trabecular meshwork tissue 102. Next, the synthetic eye model of the present disclosure includes an eye core 104 that includes many anatomical features, such as a scleral spur landmark, the back wall of Schlemm's canal, and an attachment for the synthetic trabecular meshwork. The synthetic eye model can further include an eye shell 106 configured to provide support for the eye core and provide cannula access through either a synthetic cornea or through an open design. In some embodiments, the eye shell 106 can provide an volume or chamber 103 designed and configured to represent the anterior chamber of the eye. This chamber 103 can be adjacent to the eye core 104, including the synthetic trabecular meshwork. The volume or chamber 103 can be empty (e.g., filled with air) or alternatively can be filled or injected with a fluid or substance with properties designed and configured to mimic aqueous humor in a real eye. Finally, the synthetic eye model can include an iris base 108 configured to provide a stable base and support for the eye core and to provide a visual reference for the scleral spur landmark. The synthetic eye model provided herein, when compared to a real human eye, includes proportional dimensions, realistic appearance, and realistic interactions between the cannula and ocular implant.

The synthetic trabecular meshwork tissue 102 can comprise a synthetic tissue to replicate the feel and appearance of real trabecular meshwork tissue. When the synthetic eye model 100 is fully assembled, the synthetic trabecular meshwork tissue 102 attaches to, connects to, or is stretched or wrapped around the eye core 104. In a real human eye, the trabecular meshwork is an area of tissue in the eye located around the base of the cornea, responsible for draining aqueous humor from the anterior chamber of the eye. A real trabecular meshwork tissue is "spongy" and lined by trabeculocytes which allows fluid drainage. In some examples, the synthetic trabecular meshwork tissue 102 comprises a hydrogel-based synthetic tissue material, such as SynDaver synthetic tissues, called SynTissue®.

In some embodiments, the entire synthetic model of the eye is disposable and is intended for only a limited amount of training sessions. However, in other embodiments, many components of the synthetic eye model 100 are intended to be reused for future training sessions, with components such as the synthetic trabecular meshwork tissue and/or eye core being replaceable within a reusable eye shell. For example, the eye core may be modular within the eye shell, and can be removed when the synthetic trabecular meshwork tissue is in need of replacement. A new synthetic trabecular meshwork tissue may be applied or affixed to the eye core, and re-inserted into the eye shell for additional training sessions.

The eye core 104 includes features that, in combination with the synthetic trabecular meshwork tissue 104, combines to replicate look and feel of anatomical locations in a real eye such as Schlemm's canal. As described above, in a real eye the trabecular meshwork provides for drainage of aqueous humor from the anterior chamber into Schlemm's canal. Thus, in the synthetic eye model 100, the eye core 104 includes a cutout, groove, ridge, or channel that replicates the look and feel of a real Schlemm's canal. The eye core 104, as described above, can be configured to attach or connect to the synthetic trabecular meshwork tissue. In some embodiments, the eye core 104 can include anatomical features to improve the realism of the synthetic eye model. In one example, the eye core 104 can comprise a soft material such as silicon. However, it should be understood that other materials, including materials that mimic the softness, feel, and durability of real human tissues can be used.

Figure 2:
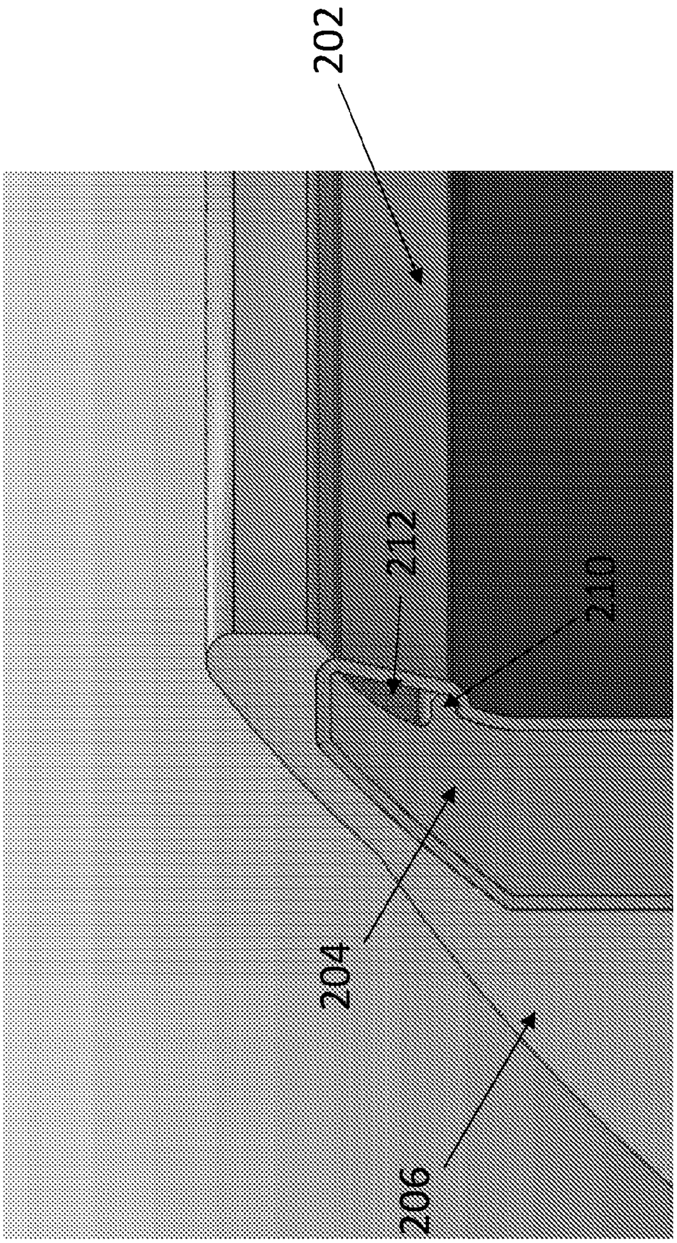
FIG. 2 is a cross-sectional view of an eye core and synthetic trabecular meshwork tissue of the synthetic eye model of FIG. 1.

FIG. 2 is a close, cross-sectional view of the synthetic eye model of FIG. 1, including the synthetic trabecular meshwork tissue 202, the eye core 204, and the eye shell 206. As shown in the cross-sectional view, the eye core 204 reveals a protrusion 210 representing a real scleral spur and a channel 212 in the eye core 204 representing Schlemm's canal of a real eye. The synthetic trabecular meshwork 202 can be stretched and/or wrapped around the eye core 204. In another embodiment, the synthetic trabecular meshwork is stretched, wrapped, or positioned only across the protrusion 210 and channel 212. Although FIGS. 1 and 2 show cross-sectional views of the eye core, it should be understood that the eye core and/or trabecular meshwork tissue can be designed and configured to encircle the full 360 degrees around the iris base of the synthetic eye model. As shown in FIG. 2, the synthetic trabecular meshwork tissue 202 is coupled to and surrounds the eye core 204, including spanning from the protrusion 210 (representing the scleral spur) across the channel 212 representing Schlemm's canal. The synthetic trabecular meshwork tissue 202 can be stretched across the channel and the protrusion so as to form an open space within the channel 212 that replicates the natural anatomical structure of Schlemm's canal and the trabecular meshwork in a real human eye.

The eye core 104 (and 204 in FIG. 2) can be modular in design and is intended to be fitted or inserted into the eye shell 106. In some embodiments, the synthetic trabecular meshwork tissue 102, the eye core 104, and the iris base 106 can all be removable from the eye shell 108, either individually or interconnected. In one embodiment, the eye core 104/204 can be a single piece configured to encircle the full 360 degrees around the iris base of the synthetic eye model. However, in other embodiments, the eye core can comprise multiple pieces that join, connect, or abut one another to form the full 360 degree component as shown.

Referring back to FIG. 1, the eye shell 106 can be a rigid, semi-rigid material, or soft material configured and designed to hold and support the other components of the synthetic eye model. The eye shell 106 can be shaped and configured to mimic the look and/or feel of the cornea and/or sclera of a real human eye. In one embodiment, the eye shell 106 can be a single piece, but in other embodiments a synthetic cornea portion can be attached or connected to a synthetic sclera portion. In one example, the eye shell 106 can comprise a soft material such as silicon. However, it should be understood that other materials, including materials that mimic the softness, feel, and durability of real human tissues can be used. As described above, in some embodiments the entire synthetic eye model can be disposable and/or single or limited use. However, in other embodiments, components such as the eye shell can be re-used, and disposable elements such as the synthetic trabecular meshwork tissue can be replaced and inserted into the eye shell as needed.

The iris base 108 is configured to provide a stable base and support for the eye core and also serve as a visual reference for the scleral spur of the eye core 104. The iris base can be manufactured from a synthetic material chosen to imitate the look and/or feel of a real human iris. In one example, the iris base 108 can comprise a soft material such as silicon. The iris base 108 can be shaped and sized to hold or be connected or attached to the eye core 104 and/or the eye shell 106. During surgical training, the iris base can be used as a landmark to help the trainee/surgeon identify the location of the scleral spur.

Figure 3B:
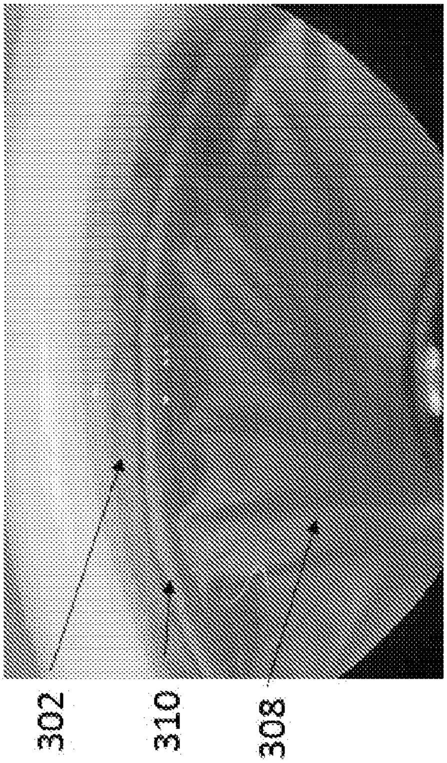
FIGS. 3A-3B are view of a synthetic eye model.
Figure 3A:
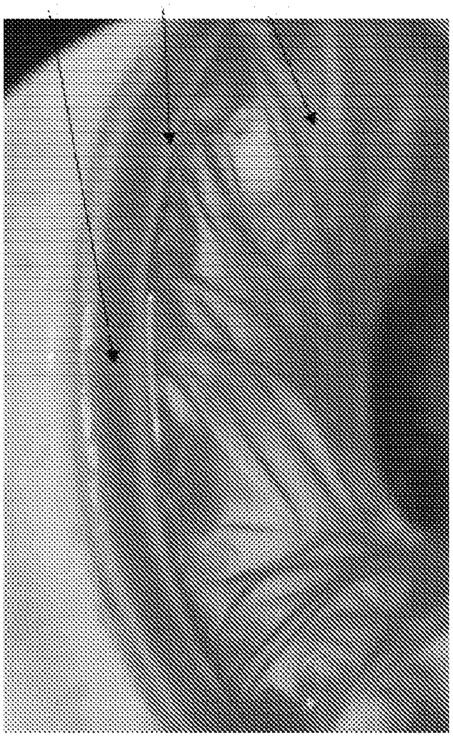

FIGS. 3A-3B are additional views of the synthetic eye model, showing the distinction between the synthetic trabecular meshwork 302, the scleral spur 310 of the eye core, and the iris base 306, as described above. It can be seen from FIGS. 3A-3B that the iris base 308 serves the important function of imitating the look of the human iris, but also providing the important visual contrast between the trabecular meshwork so as to identify the scleral spur, which is necessary for properly placing a delivery cannula within Schlemm's canal. The only difference between the two eye models in FIG. 3A and FIG. 3B are the techniques used to dye the canal/trabecular meshwork tissues, which will be described below.

Figure 4B:
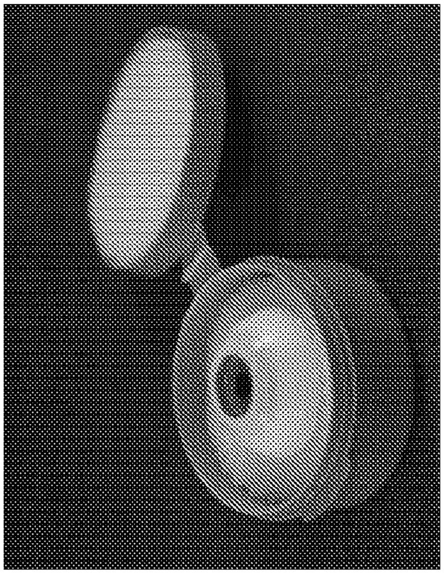
FIG. 4B illustrates an embodiment of the synthetic eye model without a synthetic cornea, for an "open sky" approach.
Figure 4A:
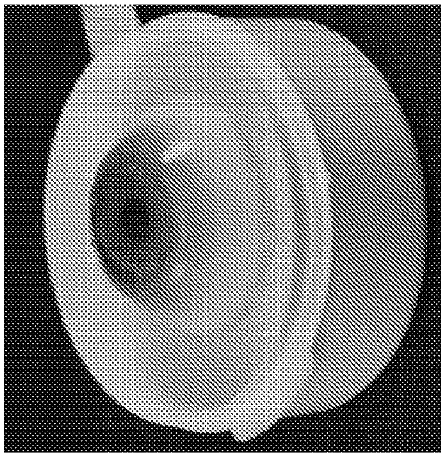
FIG. 4A illustrates an embodiment of the synthetic eye model with a synthetic cornea.

FIG. 4A illustrates a first configuration of a synthetic eye model which, in addition to the features described above, further includes a synthetic cornea that requires the use of an incision and a gonio lens to replicate the access and visualization method used in real surgery. In contrast, the a second configuration is illustrated in FIG. 4B, which represents an "open sky" approach without a synthetic cornea, allowing surgeons to directly visualize the trabecular meshwork and practice the cannula entry into Schlemm's canal without the need for the additional surgical steps of penetrating the cornea. As described above, in the first embodiment shown in FIG. 4A, the eye shell of the synthetic eye model can include the synthetic cornea, in either a one piece or two piece configuration. However, in FIG. 4B, the eye shell can include only a portion representing the sclera of the eye, with the cornea portion "missing" or removed for purposes of training.

As shown in both FIGS. 4A and 4B, the synthetic eye model can be packaged in a portable case for ease of shipping or transport. The case can include, for example, a hinged lid to allow ease of access to the synthetic eye. The design refinements needed for the synthetic eye model included molding modifications for reduction in flash, improved tissue quality control, and packaging design to maintain moisture in the tissue. Each synthetic eye model can be individually packaged in a sealed plastic container to retain moisture, keeping the synthetic trabecular meshwork tissue hydrated and realistically simulating the feel of a human trabecular meshwork.

Figure 5:
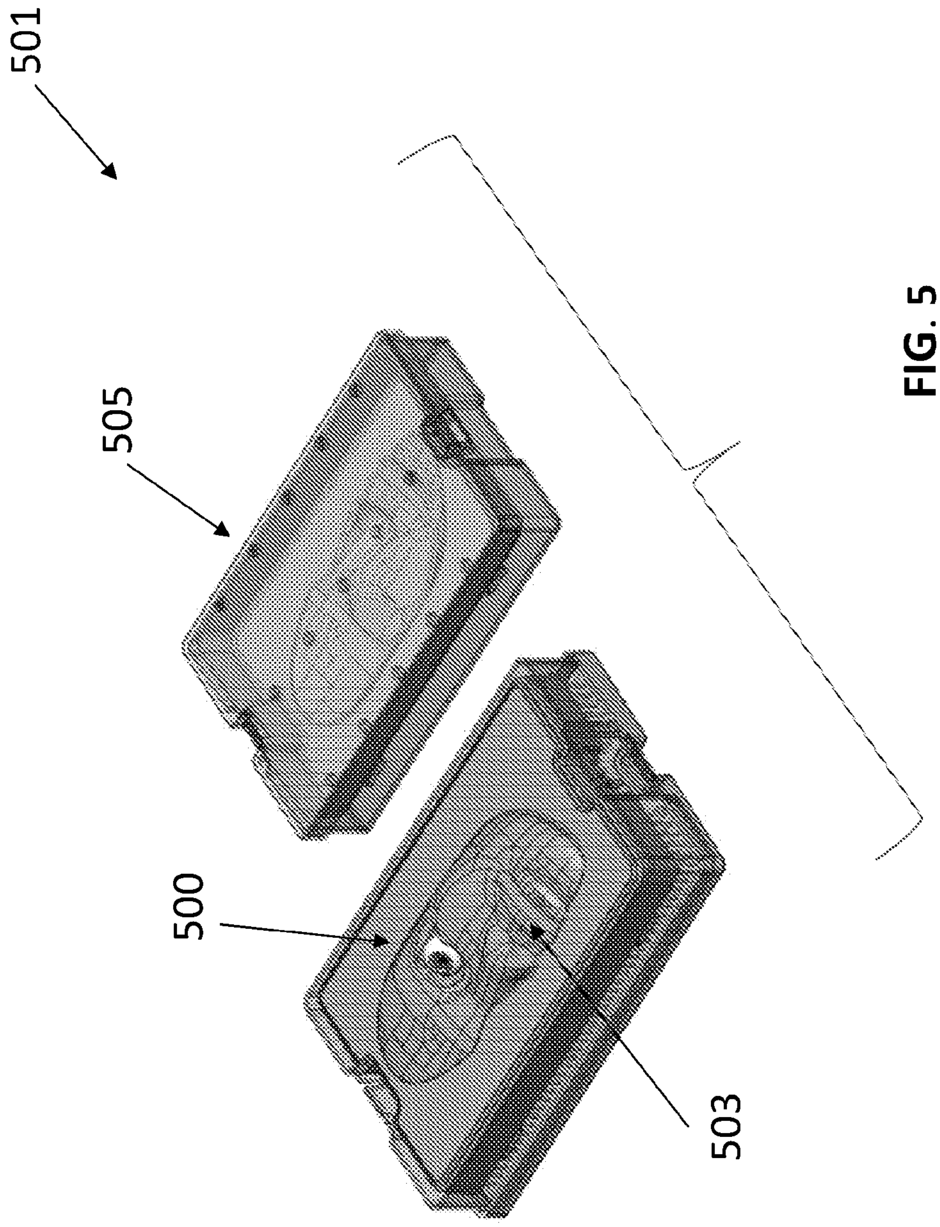
FIG. 5 illustrates one embodiment of a synthetic eye model packaged in a representation of a human face.

Referring to FIG. 5, a surgical training kit 501 can include the synthetic eye model 500 described herein inserted into a contoured tray 503 that represents a human face. The tray can fit into an instrument case 505 that serves as a convenient carrying case for various instruments, devices, and materials needed to complete the training. In one embodiment, the instrument case 505 can include a top half and a bottom half that close and seal together to protect the synthetic eye model 500 and the contoured tray 503. In use, the instrument case can be opened, exposing the synthetic eye model and contoured tray.

Figure 6:
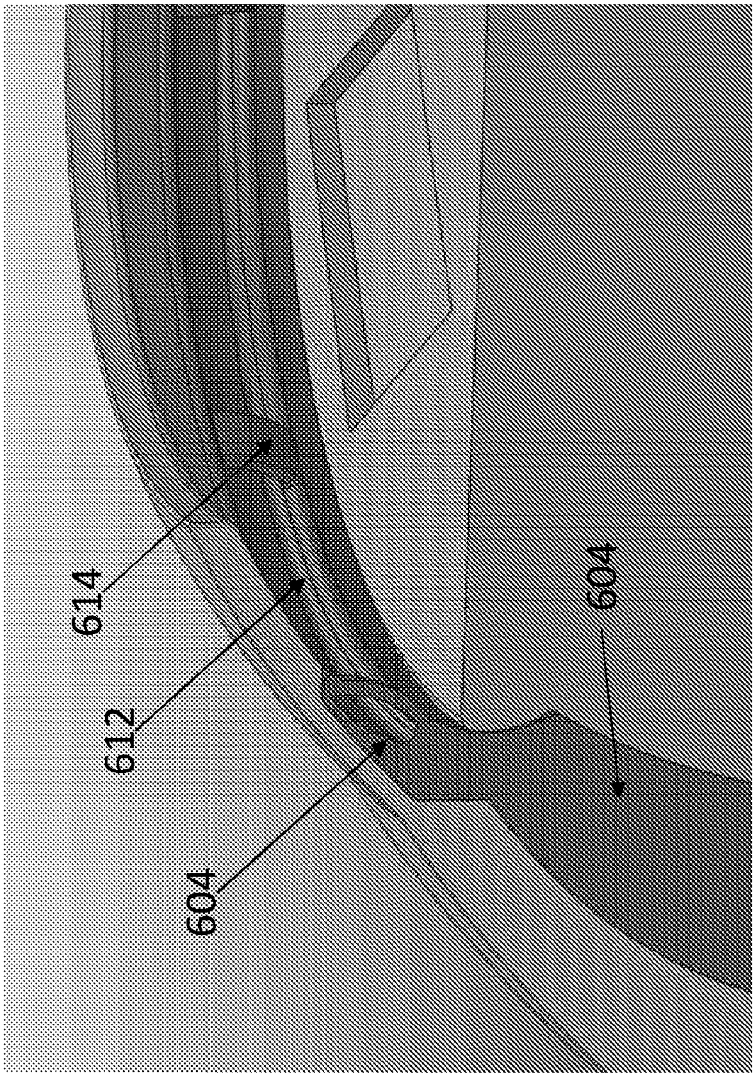
FIGS. 6 and 7 illustrate alternative embodiments of an eye core of a synthetic eye model.
Figure 7:
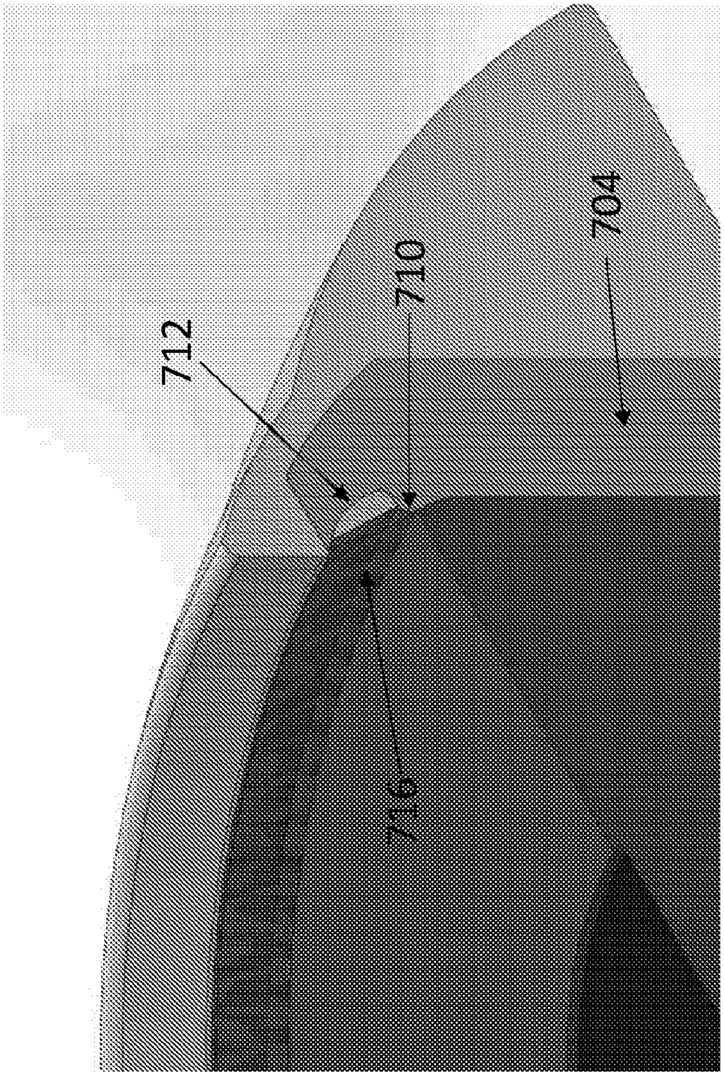

Alternative embodiments of the eye core and synthetic trabecular meshwork tissue are shown in FIGS. 6 and 7. Referring to FIG. 6, eye core 604 can include internal supports 614 configured to attach to a synthetic or real human trabecular meshwork tissue. The internal supports 614 can span or extend across the channel 612 of the eye core 604 to prevent the synthetic trabecular meshwork tissue from collapsing into the channel. Any number of internal supports can be used, depending on the material used for the eye core and the material used for the synthetic trabecular meshwork. In this embodiment, the synthetic or human trabecular meshwork tissue can be removed and/or replaced onto the eye core 604 as needed. It should be noted that in this embodiment, the eye core 604 includes a representation of Schlemm's canal, but the scleral spur landmark is not as pronounced as the embodiment of FIG. 2. It should be understood that this embodiment can also include the scleral spur landmark or protrusion as described above in FIG. 2.

Referring to FIG. 7, another embodiment of an eye core 704 includes the scleral spur landmark as represented by protrusion 710, and the channel 712 configured and shaped to represent Schlemm's canal. However, in this embodiment, a two-part gel adhesive 716 can be injected, placed, or inserted into the channel 712 to represent both the trabecular meshwork and Schlemm's canal. In this embodiment, a first gel adhesive is inserted into the channel with properties designed and configured to mimic the feel of Schlemm's canal, and then a second gel adhesive is applied on top of the first gel adhesive with properties designed and configured to mimic the feel of the trabecular meshwork. Contrary to the prior embodiments described above in which a synthetic trabecular meshwork is stretched or wrapped around the eye core, in this embodiment the synthetic material is injected into or placed within the channel of the eye core.

In some examples, the canal or channel portion within the eye core of the synthetic eye representing Schlemm's canal can be dyed to highlight the synthetic trabecular meshwork tissue as a further visual aid for the surgical training. In one embodiment, the canal is dyed with a raw silicone dye that is uncured and injected into the canal after assembly of the synthetic eye model. The uncured silicone dye does not dissipate over time since the hydrogel-based synthetic tissue of the trabecular meshwork only absorbs water, and the silicone of the eye core is hydrophobic. With this dye and method, the silicone dye stays in the canal and the area of tissue over the scleral spur landmark in the eye core remains clear. The synthetic eye model on the left of FIG. 3 illustrates a canal dyed with this technique.

In another embodiment a different dye mixture of larger dye particles is suspended in a gel like mixture of propylene glycol, glycerine, and iron oxide. The mixture is unique because the iron oxide particles are large and get stuck in the hydrogel much similar in appearance to a real human trabecular meshwork. Instead of being a solid brown line, the trabecular meshwork looks textured and speckled, making the synthetic tissue look remarkably realistic. Over time the iron oxide particles appear to maintain their position and concentration in the synthetic tissue. The synthetic eye model on the right of FIG. 3 illustrates a canal dyed with this technique.

As described above, the synthetic eye model can be used for surgical training to mimic the feel of inserting an ocular implant into Schlemm's canal. In some embodiments, the ocular implant can be sized and shaped to fit within Schlemm's canal (or within the channel of the synthetic eye model). The ocular implant can include a curved body that can be generally tubular in shape and can include one or more openings along its length. In some embodiments, the ocular implant is designed and configured to reside fully within Schlemm's canal (or the synthetic Schlemm's canal). In other embodiments, the ocular implant can include an inlet portion that is designed and configured to extend from Schlemm's canal into the anterior chamber.

The ocular implants used for surgical training with the synthetic eye model typically will require or incorporate a delivery system. The delivery system can be configured to advance the ocular implant into the eye of a patient, or in this case, into the synthetic eye model. Typically, these ocular implant delivery systems will include a cannula configured to house the ocular implant and an advancement system or mechanism configured to push or advance the ocular implant out of the cannula or into the eye (or synthetic eye). In some embodiments, the delivery system can include features that improve the ease of use, including, for example, cutting distal portions on the cannula for insertion into the eye and/or rotation features or curvature designed and configured to facilitate proper orientation with between the cannula and the target tissue (e.g., Schlemm's canal).

Figure 8:
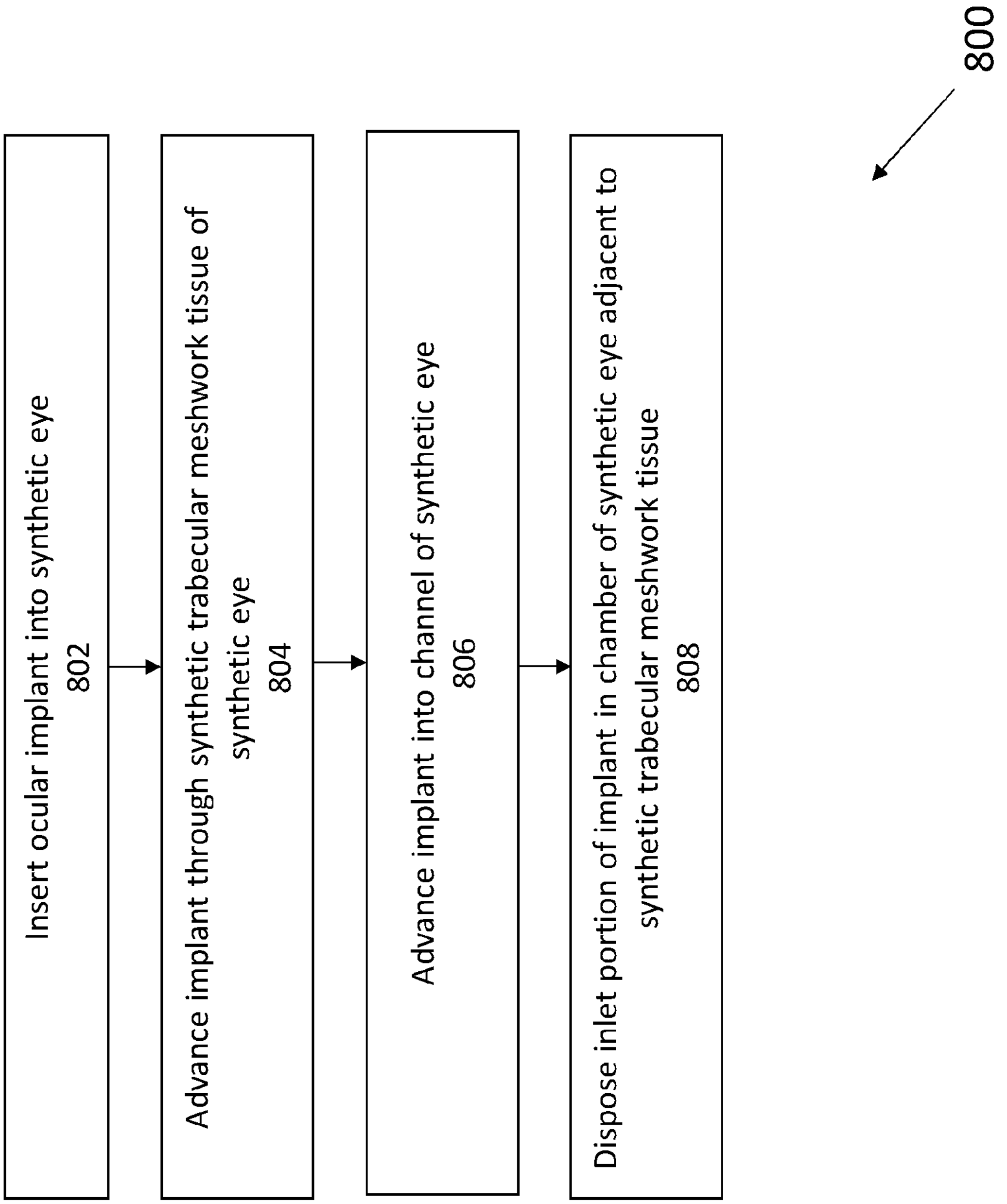
FIGS. 8-9 illustrate methods of performing surgical training on a synthetic eye.

Methods of use are also provided herein. FIG. 8 is a flowchart 800 that describes a method performing surgical training. At step 802, the method can include inserting an ocular implant into a synthetic eye. This method step can include, for example, inserting the ocular implant through an eye shell of the synthetic eye. The eye shell can include a corneal portion and/or a scleral portion. In one embodiment, the ocular implant is inserted through the corneal portion into a chamber of the synthetic eye. As described above, any type of ocular implant can be used with the synthetic eye, but in some embodiments the synthetic eye is suited for ocular implants that are designed and configured to be inserted into Schlemm's canal of a human eye. In one example, the ocular implant comprising an inlet portion at a proximal end and a Schlemm's canal portion disposed distal to the inlet portion.

Next, at step 804, the method can include advancing the Schlemm's canal portion of the implant through a synthetic trabecular meshwork tissue. At step 806, the method can include advancing the Schlemm's canal portion of the implant into a channel of the synthetic eye, so that the Schlemm's canal portion tracks the channel as it is advanced. As described above, the synthetic trabecular meshwork tissue can be stretched or extended across a channel of the eye core. In some examples, the synthetic meshwork tissue stretches across a protrusion representing the scleral spur and across the channel.

Finally, at step 806, the method can include disposing the inlet portion of the implant in a chamber of the synthetic eye adjacent to the synthetic trabecular meshwork tissue. As described above, the chamber of the synthetic eye can be designed and configured to represent an anterior chamber of a human eye. In this method, the inlet or proximal portion of the ocular implant is implanted so as to remain within the chamber of the synthetic eye, while the Schlemm's canal or distal portion of the implant is implanted to remain with the channel of the synthetic eye.

Figure 9:
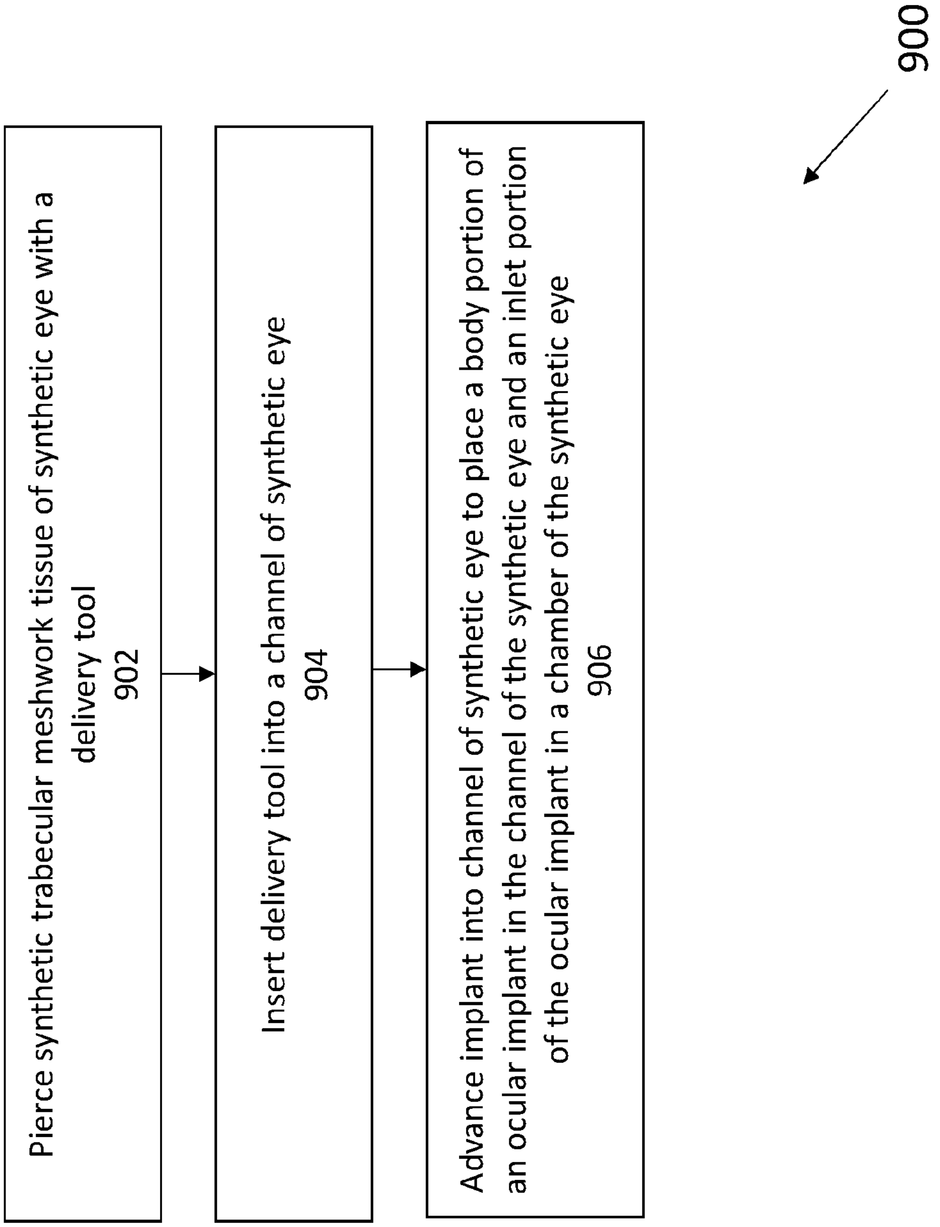

FIG. 9 is a flowchart 900 that describes a method performing surgical training. method of deploying an ocular implant into a synthetic eye. Referring to step 902, the method can include piercing a synthetic trabecular meshwork with a distal tip of a delivery tool from within a chamber of the synthetic eye. As described above, the delivery tool can include a cannula. In some embodiments, the cannula can include a distal tip designed and configured to pierce tissue. The tip can be sharp or a cutting tip, for example.

At step 904, the method can further include inserting the distal tip of the delivery tool into a channel of the synthetic eye. As described above, the channel of the eye core can be designed and configured to mimic the characteristics and dimensions of a real Schlemm's canal.

Finally, at step 902, the method can include advancing an ocular implant from the delivery tool to place a body portion of the ocular implant in the channel and an inlet portion of the ocular implant in the chamber. As described above, in some embodiments the ocular implant can include an inlet portion designed and configured to remain within the anterior chamber of the eye when the distal or body portion of the implant is inserted into Schlemm's canal, to facilitate the removal of aqueous humor from the anterior chamber.

Definitions of certain terms are provided below and shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same or substantially the same function or result). In many instances, the terms "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or able to be arranged with each other to form other additional embodiments or to complement and/or enrich the described embodiment(s), as would be understood by one of ordinary skill in the art.

It is to be understood that even though numerous characteristics of various embodiments have been set forth in the foregoing description, together with details of the structure and function of various embodiments, this detailed description is illustrative only, and changes may be made in detail, especially in matters of structure and arrangements of parts illustrated by the various embodiments to the full extent indicated by the broad general meaning of the terms in which the appended claims are expressed.

What is claimed is:

1. A synthetic eye model, comprising:

an eye shell;

a synthetic iris base positioned within the eye shell;

an eye core positioned within the eye shell and encircling the synthetic iris base, the eye core including a channel integral to the eye core configured to replicate Schlemm's canal of a human eye, and the eye core further comprising a protrusion adjacent to the channel, the protrusion configured to replicate a scleral spur of the human eye; and a synthetic trabecular meshwork tissue coupled to the eye shell and extending across the channel.

2. The synthetic eye model of claim 1, further comprising a synthetic cornea disposed over the eye shell.

3. The synthetic eye model of claim 1, wherein the synthetic trabecular meshwork tissue extends across the protrusion and the channel.

4. The synthetic eye model of claim 1, wherein the synthetic trabecular meshwork tissue comprises a hydrogel-based synthetic tissue.

5. The synthetic eye model of claim 1, wherein the eye shell includes a corneal portion and a scleral portion.

6. The synthetic eye model of claim 5, wherein the corneal portion is integral to the scleral portion.

7. The synthetic eye model of claim 1, wherein the eye core comprises a plurality of eye core pieces.

8. A synthetic eye model, comprising:

an eye shell;

a synthetic iris base positioned within the eye shell;

an eye core positioned within the eye shell and encircling the synthetic iris base, the eye core including a channel integral to the eye core configured to replicate Schlemm's canal of a human eye; and a synthetic trabecular meshwork tissue coupled to the eye shell and extending across the channel, wherein the synthetic trabecular meshwork tissue comprises a hydrogel-based synthetic tissue.

9. The synthetic eye model of claim 8, further comprising a synthetic cornea disposed over the eye shell.

10. The synthetic eye model of claim 8, wherein the eye core comprises a plurality of eye core pieces.

11. The synthetic eye model of claim 8, further comprising one or more internal supports configured to attach to the synthetic trabecular meshwork tissue to prevent the synthetic trabecular meshwork tissue from collapsing into the channel.

12. A synthetic eye model, comprising:

an eye shell;

a synthetic iris base positioned within the eye shell;

an eye core positioned within the eye shell and encircling the synthetic iris base, the eye core including a channel integral to the eye core configured to replicate Schlemm's canal of a human eye, and wherein the eye core comprises a plurality of eye core pieces; and a synthetic trabecular meshwork tissue coupled to the eye shell and extending across the channel.

13. The synthetic eye model of claim 12, further comprising a synthetic cornea disposed over the eye shell.

14. The synthetic eye model of claim 12, further comprising one or more internal supports configured to attach to the synthetic trabecular meshwork tissue to prevent the synthetic trabecular meshwork tissue from collapsing into the channel.

* * * * *